United States Patent [19]

Appel

[11] Patent Number: 5,473,953
[45] Date of Patent: Dec. 12, 1995

[54] DEVICE FOR INSPECTING VESSEL SURFACES

[75] Inventor: D. Keith Appel, Aiken, S.C.

[73] Assignee: The United States of America as represented by the United States Department of Energy, Washington, D.C.

[21] Appl. No.: 88,534

[22] Filed: Jul. 9, 1993

[51] Int. Cl.[6] .................................................. G01M 19/00
[52] U.S. Cl. ............................ 73/866.5; 73/635; 324/220
[58] Field of Search ................................ 73/866.5, 865.8, 73/865.9, 635, 637, 638; 340/856.2; 324/220, 262

[56] References Cited

U.S. PATENT DOCUMENTS

| | | | |
|---|---|---|---|
| 3,682,265 | 8/1972 | Hiraoka et al. | 73/635 X |
| 3,844,164 | 10/1974 | Romere | 73/637 |
| 3,934,457 | 1/1976 | Clark et al. | 73/637 |
| 3,999,423 | 12/1976 | Tyree | 73/635 |
| 4,108,004 | 8/1978 | Murakami | 73/866.5 |
| 4,624,026 | 11/1986 | Olson et al. | 15/340.4 |
| 4,843,895 | 7/1989 | Harper et al. | 73/865.9 |
| 4,909,091 | 3/1990 | Ellmann et al. | 73/866.5 |
| 4,962,660 | 10/1990 | Dailey et al. | 73/865.8 X |
| 4,995,320 | 2/1991 | Sato et al. | 73/638 X |
| 5,045,118 | 9/1991 | Mason et al. | 134/21 |

FOREIGN PATENT DOCUMENTS

| | | | |
|---|---|---|---|
| 484701 | 5/1992 | European Pat. Off. | 73/865.8 |
| 3818853 | 12/1989 | Germany | 73/866.5 |
| 250553 | 11/1986 | Japan | 73/866.5 |
| 57974 | 2/1990 | Japan | 73/866.5 |

*Primary Examiner*—Thomas P. Noland
*Attorney, Agent, or Firm*—Brian R. Tumm; Harold M. Dixon; William R. Moser

[57] ABSTRACT

A portable, remotely-controlled inspection crawler for use along the walls of tanks, vessels, piping and the like. The crawler can be configured to use a vacuum chamber for supporting itself on the inspected surface by suction or a plurality of magnetic wheels for moving the crawler along the inspected surface. The crawler is adapted to be equipped with an ultrasonic probe for mapping the structural integrity or other characteristics of the surface being inspected. Navigation of the crawler is achieved by triangulation techniques between a signal transmitter on the crawler and a pair of microphones attached to a fixed, remote location, such as the crawler's deployment unit. The necessary communications are established between the crawler and computers external to the inspection environment for position control and storage and/or monitoring of data acquisition.

17 Claims, 2 Drawing Sheets

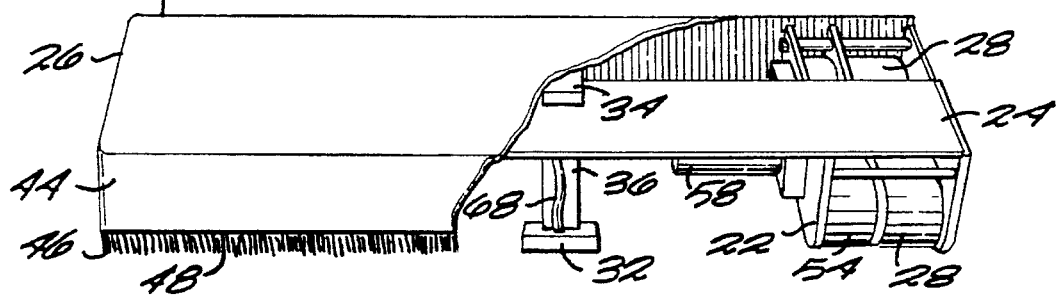
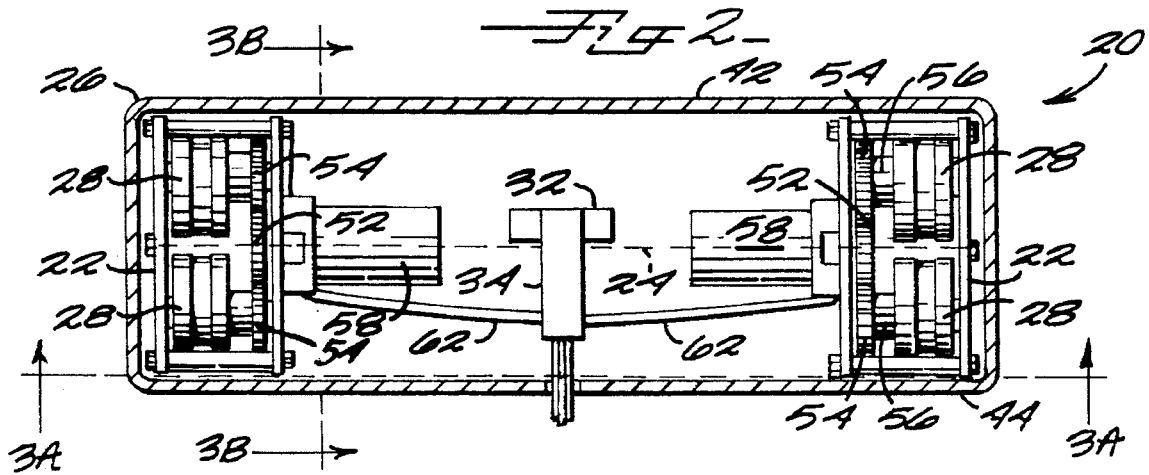
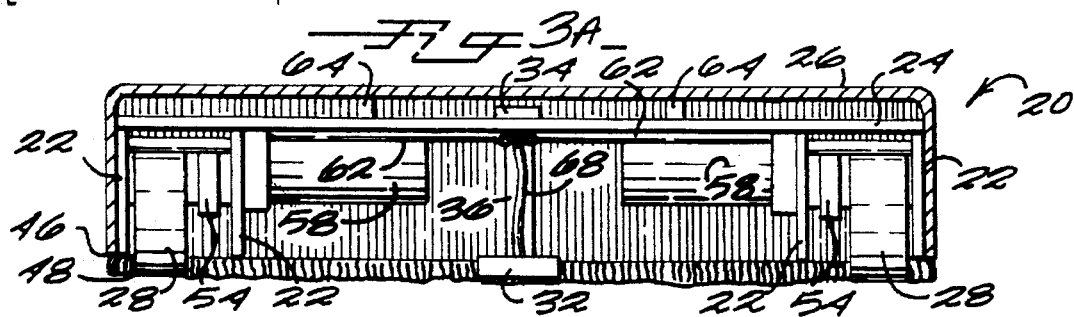
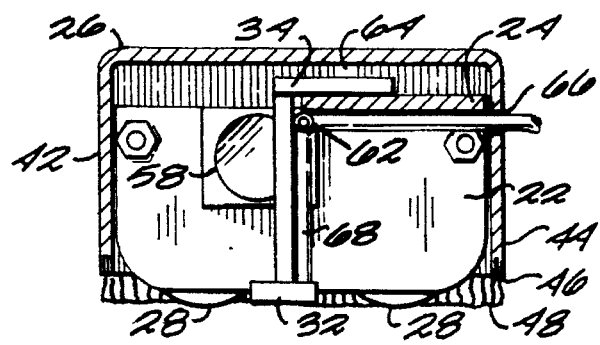

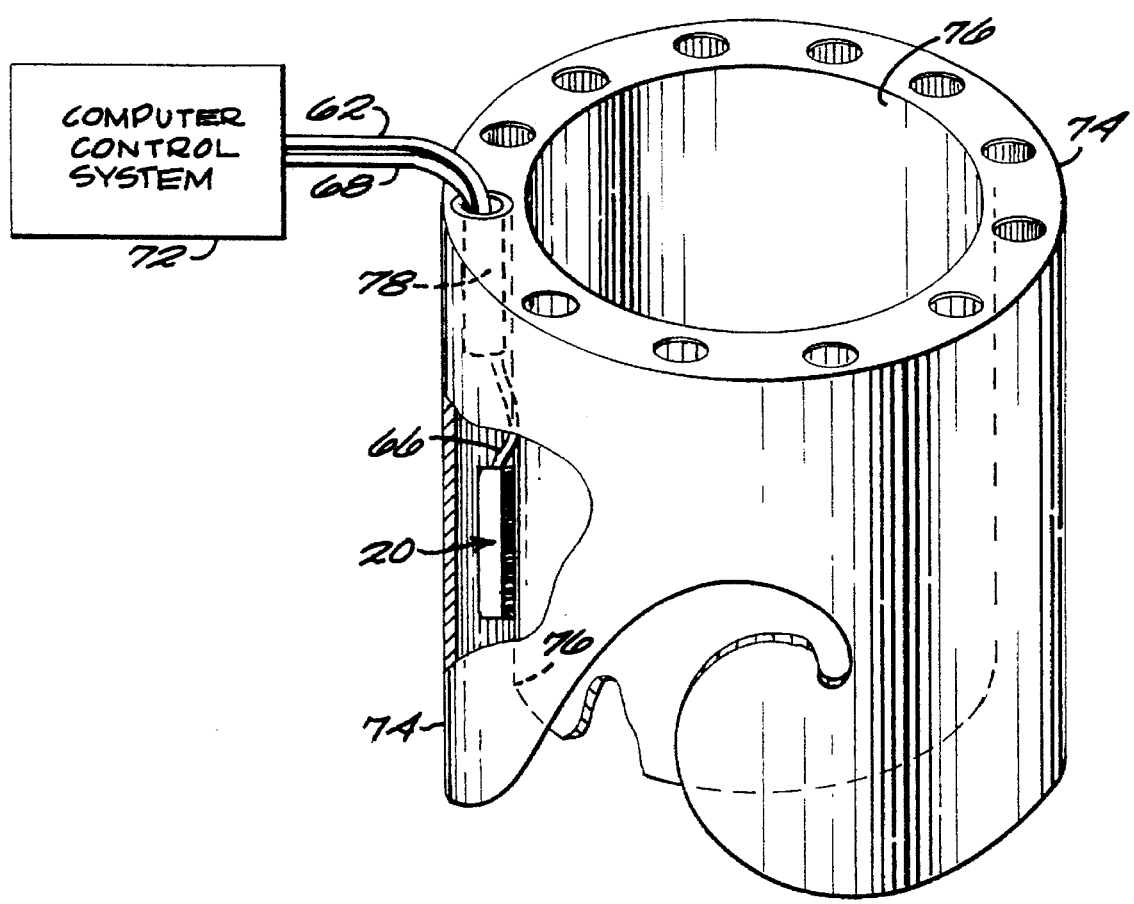

DEVICE FOR INSPECTING VESSEL SURFACES

BACKGROUND OF THE INVENTION

1. Field of the Invention

The present invention relates to inspecting walls of tanks, vessels and the like. More particularly, the present invention relates to an inspection vehicle, for use with a deployment unit, that moves along and inspects vessel walls. The United States Government has rights in this invention pursuant to Contract No. DE-AC09-89SR18035 between the U.S. Department of Energy and Westinghouse Savannah River Company.

2. Discussion of Background

The use of probes for inspecting pipelines, tanks, vessel surfaces and the like is well known in the art. Many U.S. patents disclose pipe crawlers and other similar vehicles used to inspect piping surfaces or vessel and tank walls. Inspection devices mounted on these vehicles include ultrasonic probes and eddy current probes that collect inspection information for later analysis or relay such information periodically to a unit located outside of the vessel or pipeline being inspected.

For example, in U.S. Pat. No. 5,025,215, Pirl describes a helically-driven device having a combination eddy current and ultrasonic testing probe attached thereto. The device features a head assembly that is fixable to the surface of the tubing by a pressure bladder, which is supplied fluid by a conduit system. The head assembly is connected to a drive motor located on an external drive frame assembly by a coaxial conduit.

Metala et al, in U.S. Pat. No. 4,856,337, discloses an inspecting apparatus in the form of a cylindrical housing assembly insertable within a tube or piping. A probe carrier, holding an eddy current probe and a plurality of ultrasonic probes, is rotatably mountable within the housing assembly and helically movable with respect to the housing.

An apparatus for traveling through piping is disclosed in U.S. Pat. No. 4,770,105, issued to Takagi et al. The apparatus features a plurality of continuous treads that are spring-biased to keep the apparatus in contact with the inner wall of the piping being inspected. The treads are driven by motors operating through transmission gearing.

Other related devices include Fluornoy (U.S. Pat. No. 4,418,574) and Beaver et al (U.S. Pat. No. 3,949,292). Fluornoy discloses a method and device for measuring wall thickness using a magnetic reluctance coil. Beaver et al disclose a pivoting inspection structure that is urged against the interior wall of piping by spring-loaded vanes.

Still another related device is the vessel examination system disclosed in U.S. Pat. No. 3,988,922 by Clark et al. The system features a remotely-controlled, instrument-carrying vehicle with motor-driven magnetic wheels to propel the vehicle along the interior surface of the vessel being inspected. For remote location determination, the vehicle uses an ultrasonic signal system employing a triangulation technique.

Despite the abundance of probe-carrying devices for piping, vessel walls and the like, it is believed that no inspection device provides continuous location and mapping capabilities and has sufficient holding power against the wall being inspected, yet is small enough to pass through piping having a diameter less than approximately 8 inches. Furthermore, it is believed that no existing inspection devices can be maneuvered sufficiently through limited-access vessels, such as underground piping or tanks.

SUMMARY OF THE INVENTION

According to its major aspects and broadly stated, the present invention is a vehicle for inspecting vessel surfaces. In particular, it is a remotely-controlled inspection crawler for use on the walls of tanks, vessels, piping and the like. The crawler can be configured to use a vacuum chamber for supporting itself on the inspected surface by suction or a plurality of magnetic wheels. The crawler carries an ultrasonic probe for mapping the structural integrity of the surface being inspected. Navigation of the crawler is achieved by triangulation between a signal transmitter on the crawler and a pair of microphones spaced apart and attached to a fixed, remote deployment unit. Communication is established between the crawler and computers external to the inspection environment for position control and monitoring data acquisition.

A major feature of the present invention is the use of vacuum pressure to hold the inspection crawler against the wall of the piping or vessel being inspected. The inspection crawler is enclosed within and connected to a vacuum chamber that causes the wheels of the crawler to maintain contact with the wall. The vacuum chamber uses a brush seal around its peripheral edge to maintain the vacuum seal with the vessel wall. The advantage of this feature is that the inspection crawler maintains contact with the vessel surface as it moves along the entire area of the surface, including vertical surfaces areas and horizontal, overhead surface areas.

Another feature of the present invention is the relatively small size of the inspection crawler, including all of its featured equipment. This feature allows the crawler to be inserted through 8" diameter access ports of tanks to inspect characteristics such as structural integrity and weld soundness. Also, it allows the inspection crawler to inspect areas where access is limited, such as underground vessels, piping and the like and hazardous areas in which larger crawlers cannot go and where human operators would be at risk.

Still another feature is the navigation system used by the inspection crawler. For the present invention, a three-point arrangement exists between the inspection crawler and the two antennae of the deployment unit that, through triangulation, can be used for identifying the location of the inspection crawler along the vessel surface. The arrangement provides continuous location information to a remotely located computer control system that, in turn, transmits movement control information to a plurality of position motors, mounted on the inspection crawler, for directing the movement of the crawler's wheels. This feature provides continuous information about the position of the inspection crawler on the surface area being inspected, thus allowing an entire surface area to be inspected systematically and a map of the structural features of the entire surface area to be generated.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a partial cut-away perspective view of an inspection crawler with a vacuum chamber shown generally

3 from the rear according to a preferred embodiment of the present invention;

FIG. 2 is a top view of the crawler of FIG. 1;

FIG. 3a is a partial cross-sectional view of the crawler taken along lines 3a–3a of FIG. 2;

FIG. 3b is a partial cross-sectional view of the crawler taken along lines 3b—3b of FIG. 2; and FIG. 4 is a schematic diagram of the crawler of FIG. 1 shown in use along a tank wall.

DETAILED DESCRIPTION OF A PREFERRED EMBODIMENT

In the following description, similar components are referred to by the same reference numeral in order to simplify the understanding of the sequential aspect of the drawings and the symmetric nature of the device.

Referring now to FIG. 1, the inspection crawler 20 in its preferred embodiment is a pair of drive modules 22 (only one shown in FIG. 1) spaced apart and connected to a generally horizontal mounting plate 24. A rectangular vacuum chamber 26 covers both drive modules 22 and mounting plate 24. Each drive module 22 has a plurality of wheels 28 rotatably mounted therein, preferably two wheels aligned and positioned so that their respective axes of rotation are parallel with respect to each other. Vacuum chamber 26 is attached to mounting plate 24 and dimensioned so that vacuum to chamber 26 just covers drive modules 22 with minimal spacing around mounting plate 24 and drive modules 22.

Approximately midway between drive modules 22, an inspection probe 32 extends below mounting plate 24 and connects to mounting plate 24 via a horizontal mounting arm 34 connected to mounting plate 24 and a vertically extending arm 36. Thus, inspection probe 32, as mounted, is held just above the vessel surface being inspected. Mounting plate 24, which is preferably made of aluminum but can be made from any suitable material, is adapted for carrying other equipment in addition to inspection probe 32, such as inspection cameras.

Horizontal mounting arm 34 attaches to the top of mounting plate 24 and extends slightly in front of mounting plate 24, that is, closer toward a front side 42 of crawler 20 than a rear side 44 of crawler 20, "front" being defined as the lead side of crawler 20 when proceeding in the usual direction of travel. In this manner, vertical extending arm 36 positions inspection probe 32 toward front side 42 of crawler 20.

Vacuum chamber 26 preferably has a peripheral edge 46 that contacts the surface of the vessel being inspected. Peripheral edge 46 has a brush seal 48, which is a movable seal that restricts air flow between peripheral edge 46 and the vessel surface so that crawler 20 can hold a sufficient vacuum seal to support itself by suction to the vessel surface while moving. In this manner, brush seal 48 allows vacuum chamber 26, and thus crawler 20, to maintain constant contact with the vessel surface, even when wheels 28 rotate to move crawler 20 along the vessel surface.

As shown in FIGS. 2, 3a and 3b, each drive module 22 includes preferably a pair of rotatably mounted wheels 28. Wheels 28 can be made of any suitable material, but are preferably a lightweight material, such as polyurethane, when used in vessels having non-ferromagnetic walls. Alteratively, when crawler 20 is used in vessels having ferromagnetic walls, wheels 28 are made from a high energy magnetic material to assisting crawler 20 in supporting itself magnetically the vessel walls.

Also, each drive module 22 houses a gear train 52 for driving wheels 28. Each gear train 52 preferably comprises a plurality of gears 54 corresponding to and in rotational connection with wheels 28 through a common axle 56 connected therebetween. Gear trains 52 are in rotatable connection with gears 54 through an interlocking mesh of teeth radially displaced on both gear train 52 and gears 54.

Each gear train 52 is controlled by and operationally connected to a positioning motor 58 mounted on the inner wall of drive module 22. Each positioning motor 58 is controlled by electrically conducting wiring 62 (discussed below in further detail) connected thereto and attached along the underside of mounting plate 24.

Vacuum chamber 26 is dimensioned slightly longer than mounting plate 24, slightly deeper than drive modules 22 and slightly taller than mounting plate 24 mounted on drive modules 22 so that, when mounted properly, vacuum chamber 26 just covers mounting plate 24 and drive modules 22, as shown best in FIG. 3a. A plurality of vertical mounts 64 connects vacuum chamber 26 to the top of mounting plate 24 so that vacuum chamber 26 is raised slightly off of mounting plate 24.

Electrically conductive wiring 62 is mounted to the underside of mounting plate 24 and establishes electrical connection with positioning motors 58 for controlling the operation of positioning motors 58. Wiring 62 runs from positioning motors 58 along the underside of mounting plate 24 and through a sealed opening 66 (best seen in FIGS. 2, 3b) formed in rear side 44 of vacuum chamber 26. Also, a second set of electrically conducting wiring 68 establishes electrical connection with inspection probe 32 for transmitting data produced by inspection probe 32. Preferably, second wiring 68 runs from inspection probe 32 along vertical extending arm 36 to the underside of mounting plate 24 and through sealed opening 66.

Positioning motors 58 control the rotation of each of gear trains 52 independently so that wheels 28 can be rotated accordingly to steer crawler 20 efficiently. That is, by rotating one of gear trains 52 slightly more than the other of gear trains 52, wheels 28 can be rotated in a manner that changes the direction crawler 20 is moving, much like the steering of any tracked vehicle.

Referring to FIG. 4, wiring 62 and second wiring 68 from crawler 20 runs through sealed opening 66 preferably to a computer control system 72. Preferably, computer control system 72 is located external to a vessel 74 having a surface or wall 76 being inspected by crawler 20. Preferably, a deployment unit 78 attaches to vessel 74 and assists in routing wiring 62, 68 from sealed opening 66 of crawler 20 to computer control system 72.

Preferably, computer control system 72 is programmed to identify continuously the location of crawler 20 along wall 76 of vessel 74 based on information received from crawler 20. Also, computer control system 72 is equipped with a feedback system that, through the identification of the location of crawler 20 along wall 76 of vessel 74, controls the operation of positioning motors 58 so that crawler 20 can be steered and moved in the desired direction.

The location of crawler 20 along wall 76 of vessel 74 is identified preferably by triangulation. In this manner, crawler 20 preferably has means for emitting a continuous signal that is detected preferably by a pair of microphones attached at two spaced-apart locations, for example, at opposite ends of deployment unit 78 or at two known locations on wall 76 of vessel 74. A triangle is defined by crawler 20 and each of the two microphones.

The distance of crawler 20 from each of the two microphones can be determined based on the time required for each of the two microphones to receive a signal emitted from crawler 20. Using these two distances and the known distance between the two microphones, a triangle is defined with the length of all three sides known. By knowing the fixed locations of the two microphones, the location of crawler 20 along wall 76 of vessel 74 can be determined from the basic geometric relationships between crawler 20 and the two microphones. It is understood that variations of triangulation, as well as other location identification methods, can be substituted for the preferred location method, as just described, without departing from the spirit of the invention.

In use, crawler 20 in positioned in close proximity to wall 76 of vessel 74, for example, by deployment unit 78 or other appropriate means. Brush seal 48 created by peripheral edge 46 keeps wheels 28 of crawler 20 in contact with wall 76. Also, crawler 20 is maintained against walls 76 by wheels 28 because walls 76 will then be made of a ferromagnetic material and wheels 28 are made of a magnetic material, as discussed above. Thus, crawler 20 can travel along walls 76 of vessel 74 without regard to the orientation of walls 76, including walls that are generally vertical and walls that require crawler 20 to be inverted.

Positioning motors 58 operate gear trains 52 per instructions from computer control system 72 through wiring 62. Accordingly, gears 54 rotate wheels 28 in the manner previously described so that crawler 20 travels across wall 76 of vessel 74 in the desired direction and with the desired motion.

Despite the vacuum seal created by brush seal 48 between crawler 20 and wall 76 of vessel 74, the coefficient of friction of wall 76 with respect to brush seal 48 is preferably lower than the coefficient of friction of wall 76 with respect to wheels 28. Thus, wheels 28 have sufficient traction so that the rotation of wheels 28 overcomes the drag of brush seal 48 and moves crawler 20 along wall 76 of vessel 74 even though peripheral edge 46 maintains contact with wall 76 of vessel 74.

During the movement of crawler 20 across wall 76 of vessel 74, inspection probe 32 measures characteristics, preferably the thickness of wall 76 and the soundness of welds on wall 76, of the portion of wall 76 passing immediately beneath inspection probe 32. The information produced and recorded by inspection probe 32 is sent to computer control system 72 via second wiring 68. Preferably, inspection probe 32 provides continuous information to computer control system 72 via second wiring 68. In this manner, crawler 20 can be systematically maneuvered across wall 76 of vessel 74 so that the measured characteristics form a complete map of vessel 74.

It will be apparent to those skilled in the art that many changes and substitutions can be made to the preferred embodiment herein described without departing from the spirit and scope of the present invention as defined by the appended claims.

What is claimed is:

1. Apparatus for inspecting a surface, said apparatus for use with an inspection probe, said apparatus comprising:
    a frame adapted for carrying said inspection probe so that said inspection probe is held within an operative distance from said surface;
    means mounted to said frame for moving said frame along said surface so that said inspection probe can inspect said surface; and
    means connected to said frame for holding said apparatus in contact with said surface as said moving means moves said frame over said surface, wherein said holding means has
        a vacuum chamber formed around said frame, said vacuum chamber having a peripheral edge,
        a brush seal carried by said peripheral edge and in sealing engagement with said surface, and
        means for reducing pressure in said vacuum chamber,
    said vacuum chamber and said brush seal limiting air flow between said surface and said apparatus so that suction thereby created when said reducing means reduces pressure inside said vacuum chamber holds said apparatus to said surface,
    said moving means and said holding means cooperating to allow said apparatus to move over said surface while being held to said surface, said apparatus movable controllably in preselected directions.

2. The apparatus as recited in claim 1, wherein said moving means has sufficient traction on said surface to overcome the drag of said holding means holding said apparatus to said surface.

3. The apparatus as recited in claim 1, wherein said moving means further comprises a plurality of wheels rotatably carried by said frame.

4. The apparatus as recited in claim 1, wherein said moving means further comprises a plurality of wheels rotatably carried by said frame and a corresponding plurality of positioning motors in operative connection with said plurality of wheels.

5. The apparatus as recited in claim 1, wherein said surface is made of a ferromagnetic material and said moving means further comprises a plurality of wheels made of a magnetic material to assist said holding means in holding said apparatus to said surface.

6. Apparatus for inspecting a wall, said apparatus for use with a probe, said apparatus comprising:
    a frame;
    a plurality of wheels carried by said frame for moving said frame over said wall, said wheels being made of a magnetic material;
    means in radio communication with said frame for controlling said plurality of wheels; and
    means connected to said frame for holding said frame in contact with said wall as said plurality of wheels means moves said frame over said wall, said magnetic wheels assisting said holding means in holding said frame in contact with said wall, said holding means further comprising a vacuum chamber formed around said frame, said vacuum chamber having a peripheral edge;
    a brush seal carded by said peripheral edge and in sealing engagement with said wall; and
    means for reducing pressure in said vacuum chamber,
    said vacuum chamber and said brush seal limiting air flow between said wall and said apparatus so that suction thereby created when said reducing means reduces pressure inside said vacuum chamber holds said apparatus to said wall,
    said plurality of wheels and said holding means cooperating to allow said frame to move over said wall while being held to said wall, said controlling means moving said frame in preselected directions for preselected distances so that said probe can collect said data with respect to said wall as said frame moves.

7. The apparatus as recited in claim 6, wherein said apparatus further comprises:

means carried by said frame for transmitting a signal; and means carried by said controlling means for receiving said signal from said transmitting means, said controlling means determining the probe location from said transmitted signal.

8. The apparatus as recited in claim 6, wherein said plurality of wheels has sufficient traction on said wall to overcome the drag of said holding means holding said apparatus to said wall.

9. The apparatus as recited in claim 6, further comprising means carried by said frame for collecting data related to said wall.

10. Apparatus for inspecting the walls of a vessel, said apparatus for use with an inspection probe, said apparatus comprising:

a frame adapted for carrying said inspection probe so that said inspection probe is held within an operative distance from said vessel walls;

means mounted to said frame for moving said frame over said vessel walls;

means connected to said frame for holding said apparatus in contact with said vessel walls as said moving means moves said frame over said vessel walls, the holding means comprising, a vacuum chamber formed around said frame, said vacuum chamber having a peripheral edge;

a brush seal carded by said peripheral edge and in sealing engagement with said vessel walls; and means for reducing pressure in said vacuum chamber, said vacuum chamber and said brush seal limiting air flow between said vessel walls and said apparatus so that suction thereby created when said reducing means reduces pressure inside said vacuum chamber holds said apparatus said vessel walls, said moving means and said holding means cooperating to allow said frame to move over said vessel walls while being held to said vessel walls, said apparatus movable controllably in preselected directions; and means in communication with said apparatus for identifying the location of said apparatus on said vessel walls using triangulation.

11. The apparatus as recited in claim 10, further comprising means in radio communication with said frame for controlling said moving means.

12. The apparatus as recited in claim 10, wherein said apparatus further comprises means in radio communication with said frame for controlling said moving means and said identifying means further comprises:

means carried by said frame for transmitting a signal; and means carried by said controlling means for receiving said signal from said transmitting means, said controlling means determining said location from said transmitted signal.

13. The apparatus as recited in claim 10, wherein said moving means has sufficient traction on said vessel walls to overcome inertia and static friction of said holding means holding said apparatus to said vessel walls.

14. The apparatus as recited in claim 10, wherein said identifying means further comprises means carried by said frame for transmitting a signal and means spaced apart from said transmitting means for receiving said signal, and wherein said identifying means uses the time required for said signal to be received by said receiving means to identify the location of said apparatus on said vessel walls by triangulation.

15. The apparatus as recited in claim 10, wherein said moving means further comprises a plurality of wheels rotatably carried by said frame and a corresponding plurality of positioning motors in operative connection with said plurality of wheels.

16. The apparatus as recited in claim 10, further comprising an inspection probe carried by said frame for collecting data related to said walls of said vessel walls.

17. The apparatus as recited in claim 10, wherein said vessel walls are made of ferromagnetic material and said moving means further comprises a plurality of wheels made of a magnetic material to assist said holding means in holding said apparatus to said vessel walls.

* * * * *